US008257268B2

(12) United States Patent
MacLeod et al.

(10) Patent No.: US 8,257,268 B2
(45) Date of Patent: Sep. 4, 2012

(54) DEVICES AND SYSTEMS FOR THE PREVENTION OF SUDDEN INFANT DEATH SYNDROME (SIDS)

(76) Inventors: Ainslie MacLeod, Vashon, WA (US); Daniel David Rubens, Seattle, WA (US)

(*) Notice: Subject to any disclaimer, the term of this patent is extended or adjusted under 35 U.S.C. 154(b) by 1085 days.

(21) Appl. No.: 12/173,144

(22) Filed: Jul. 15, 2008

(65) Prior Publication Data

US 2009/0024043 A1 Jan. 22, 2009

Related U.S. Application Data

(60) Provisional application No. 60/950,179, filed on Jul. 17, 2007.

(51) Int. Cl.
*A61B 5/0205* (2006.01)
*A61B 5/01* (2006.01)
*A61B 5/04* (2006.01)
*A61B 5/08* (2006.01)
*A61F 7/00* (2006.01)
*A61M 16/10* (2006.01)

(52) U.S. Cl. ........ 600/484; 600/513; 600/529; 600/549; 607/96; 607/109; 128/203.14

(58) Field of Classification Search .......... None
See application file for complete search history.

(56) References Cited

U.S. PATENT DOCUMENTS

| 4,813,427 A * | 3/1989 | Schlaefke et al. ............ 600/484 |
| 5,800,360 A * | 9/1998 | Kisner et al. .................. 600/532 |
| 6,679,830 B2 * | 1/2004 | Kolarovic et al. ............. 600/22 |
| 6,918,770 B2 * | 7/2005 | Odiwo .......................... 434/262 |
| 2001/0044588 A1 * | 11/2001 | Mault ........................... 600/549 |
| 2005/0120459 A1 * | 6/2005 | McConnell et al. ............. 2/69.5 |
| 2005/0188992 A1 * | 9/2005 | Cockerham .............. 128/206.29 |

FOREIGN PATENT DOCUMENTS

| GB | 2277377 A | * 10/1994 |
| WO | WO 2006124696 A1 | * 11/2006 |

OTHER PUBLICATIONS

Young et al. A prospective, population-based study of the epidemiology and outcome of out-of-hospital pediatric cardiopulmonary arrest. Pediatrics, vol. 114, No. 1, pp. 157-164, Jul. 2004.*
Multiple Serotonergic Brainstem Abnormalities in Sudden Infant Death Syndrome, David S. Paterson, PhD et al., JAMA, 2006; 296:2124-2132.

* cited by examiner

*Primary Examiner* — Jennifer Dunston
(74) *Attorney, Agent, or Firm* — Gordon & Jacobson, PC

(57) ABSTRACT

Methods and systems for preventing the underlying anatomical cause that gives rise to a predisposition to SIDS are provided. Methods and systems are provided for the diagnosis of infants predisposed to SIDS. Methods and systems are provided for the therapeutic treatment of infants predisposed to SIDS. A treatment device includes an auditory stimulation system, a monitoring system, a warming system and a response system that can respond to and alleviate crisis situations.

16 Claims, 2 Drawing Sheets

DEVICES AND SYSTEMS FOR THE PREVENTION OF SUDDEN INFANT DEATH SYNDROME (SIDS)

RELATED APPLICATION

This application claims the benefit of U.S. Ser. No. 60/950,179, filed Jul. 17, 2007, which is hereby incorporated by reference herein in its entirety.

BACKGROUND OF THE INVENTION

1. Field of the Invention

This invention relates broadly to methods, devices and systems for prevention, diagnosis, and treatment of medical conditions. More particularly, this invention relates to methods, devices and systems for prevention of sudden infant death syndrome (SIDS) and for the diagnosis and treatment of infants predisposed to SIDS.

2. State of the Art

Sudden infant death syndrome (SIDS) is any sudden and unexplained death of an apparently healthy infant aged one month to one year. SIDS is responsible for roughly 0.05%, or 50 deaths per 100,000 births in the United States. It is responsible for far fewer deaths than congenital disorders and disorders related to short gestation, though it is the leading cause of death in infants that have appeared healthy after one month of age.

Very little has been known about the possible causes of SIDS, and there has been no reliable or proven method for prevention. Although studies have identified risk factors for SIDS, such as the prone sleeping position, presence of an upper respiratory infection, exposure to cigarette smoke, over-wrapping and over warming in the winter months, there has been little understanding of the syndrome's biological cause or causes.

One recent study attributes SIDS death to abnormalities in the part of the brain that helps control functions like breathing, blood pressure and arousal. Patterson et al., Multiple Serotonergic Brainstem Abnormalities in Sudden Infant Death Syndrome, *JAMA*, 296: 2124-2132 (2006). In this study, researchers examined the brains of 31 babies who had died of SIDS and 10 who had died from other causes. The study found that babies that died from SIDS had abnormalities in the brain stem which appeared to affect the ability to use and recycle serotonin. Serotonin levels are responsible for regulating mood as well as vital body functions. According to the National Institutes of Health, the new finding is the strongest evidence to date suggesting that innate differences in a specific part of the brain may place some at increased risk of dying from SIDS. A key point is that these results do not indicate how the brain differences that precipitate SIDS were incurred (whether, e.g., genetic disorder, disease), how to prevent SIDS, or how to treat a high risk infant so as to reduce or prevent infant mortality from those infants predisposed to SIDS. Additionally, this explanation does not take into account abnormalities of function found in other regions (such as to hearing) or explain why SIDS infants do not die in the first three weeks of life.

SUMMARY OF THE INVENTION

A new theory regarding the cause of SIDS is provided. This theory identifies SIDS as related to an injury at birth. This injury is the result of an acute pressure surge in the venous circulation of the birthing infant from blood transfused from the placenta via the umbilical vein to the infant at the end of the birthing process. The high pressure causes venous injury to the small end veins in delicate and critical regions (e.g., cochlear and vestibular organs and brainstem) responsible for providing the brain with correct information regarding blood $CO_2$ levels (See Appendix 1). In the context of such new theory, the following is provided.

In accord with the invention; methods, devices and systems are provided for the prevention of SIDS. In particular, methods, devices and systems are provided for preventing the underlying anatomical and physiological cause that gives rise to a predisposition to SIDS.

Also in accord with the invention, methods, devices and systems are provided for the diagnosis of infants predisposed to SIDS.

Further in accord with the invention, methods, devices and systems are provided for the therapeutic treatment of infants predisposed to SIDS.

DETAILED DESCRIPTION OF THE PREFERRED EMBODIMENTS

Figure 1:
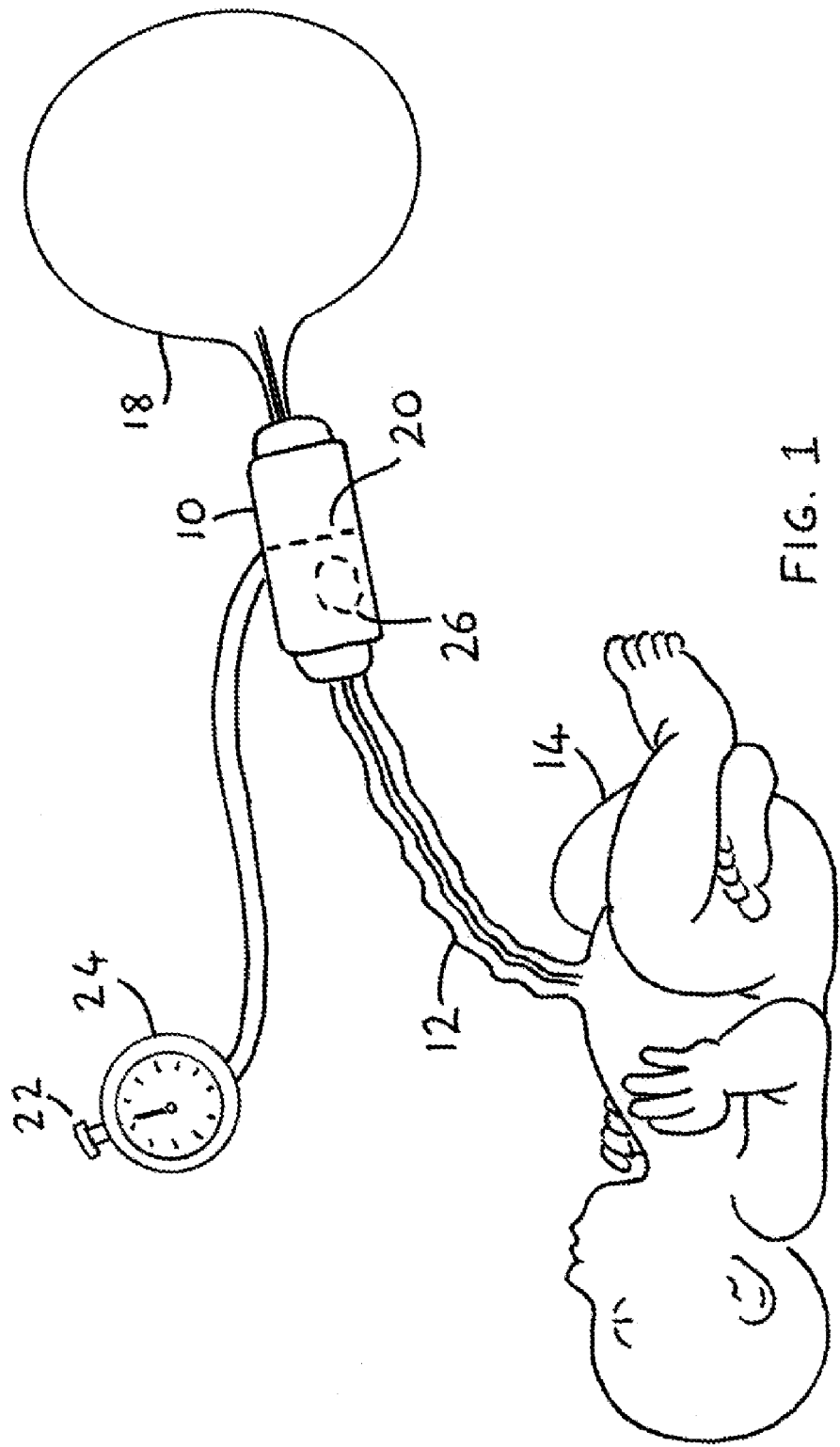
FIG. 1 illustrates a method and an embodiment of a device according to the invention for the prevention of a predisposition to SIDS.
Figure 2:
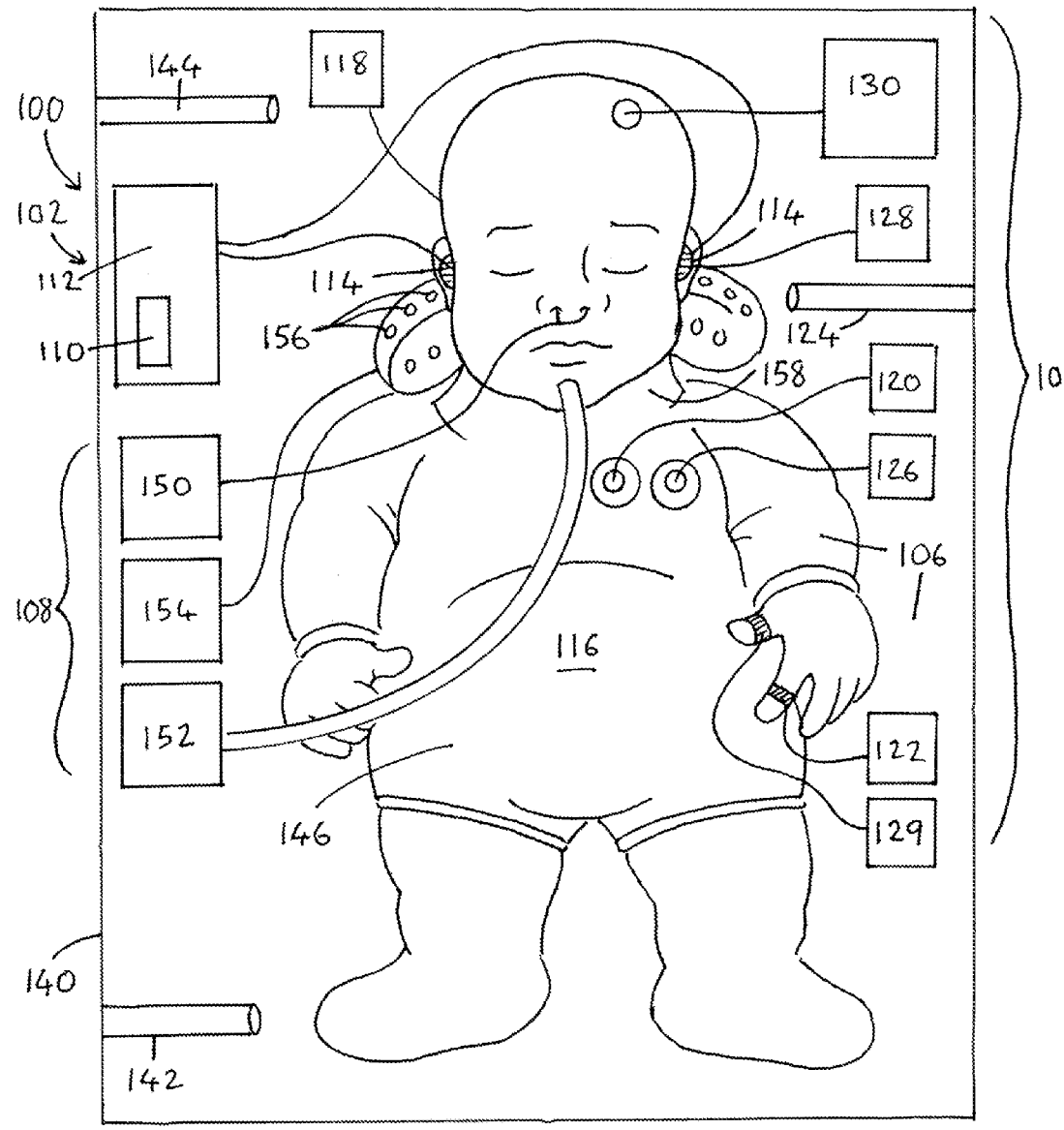
FIG. 2 illustrates an embodiment of a treatment device according to the invention for the stimulation, monitoring, warming and crisis response for an infant predisposed to SIDS.

In accord with the invention, methods, devices and systems for the prevention of SIDS are provided. In particular, methods, and a device for preventing the underlying anatomical cause that gives rise to a predisposition to SIDS are provided. Also in accord with the invention, methods for the diagnosis of infants predisposed to SIDS are provided. Further in accord with the invention, methods, a device and systems thereof are provided for the therapeutic treatment of infants predisposed to SIDS. Before describing in detail the particular methods, device and system identified above, it is helpful to provide the contextual theory on which such methods, devices and systems are based.

It is theorized by the inventors that the predisposition of an infant to SIDS results from a high pressure placental transfusion injury that occurs as an infant is delivered. During delivery of an infant, blood accumulates in the placenta under increasing pressure from the ongoing contractions of labor. Large volumes of placental blood are frequently transfused into the infant's veins at the time of delivery when the umbilical cord is straightened and before it is clamped. In the instance of an infant who may become predisposed to SIDS, pressures as high as 200-300 mm Hg are proposed to be present in the infant's veins at the time of placental transfusion.

The inner ear is particularly vulnerable to a high venous pressure insult since the veins of the inner ear are supplied directly by large carriage way veins (the internal jugular vein and inferior petrosal sinus). This contrasts with the majority of organs in the body in which the venous supply passes through increasingly smaller tributaries before supplying the organ. As a result, the small end organ veins of the inner ear rupture and exude blood into the cochlear and vestibular organs when large volumes of placental blood are pulsed under high pressure through an infant's venous system. The cochlear and vestibular organs are especially vulnerable to the effects of a high pressure venous insult since they are mutually encased within the confined space of the temporal bone and share the same venous drainage.

The high pressure injury from placental transfusion results in small vein rupture with hemorrhage and exudation in other vulnerable sites that include the pulmonary, splanchnic, renal bed as well as the small veins supplying the central $CO_2$ chemoreceptors in the brain.

Damage to type II vestibular hair cells in the cristae of the vestibular organ plays a key role in the mechanism of SIDS death since such hair cells transmit $CO_2$ information from the peripheral carotid chemoreceptors to the brain. Damage to the type II vestibular hair cells in the inner ear as well as the central chemoreceptors in the brain therefore prevents the brain from receiving correct information concerning rising $CO_2$ levels and result in catastrophic $CO_2$ accumulation.

Any of the established risk factors that include, among others, sleep, the prone sleeping position, presence of an upper respiratory infection, exposure to cigarette smoke, over-wrapping and over warming in the winter months, alterations in barometric pressure, precipitate a rise in $CO_2$ which can lead to the demise of a SIDS infant since the rise in $CO_2$ is not detected and the appropriate respiratory response (increased respiratory rate and tidal volume) as well as other survival strategies (rolling over, self arousal, etc.) cannot be implemented.

There is a greater likelihood of the venous damage occurring if there is entry of amniotic fluid into the fetal circulation prior to birth, as this will notably decrease the viscosity of the fetal blood and thereby increase the speed and force of the venous pressure injury at the time of placental transfusion.

Even with such damage infants predisposed to SIDS do not die during the first three weeks of life. Newborn babies are more able to clear rising $CO_2$ levels for the following reasons. First, fetal control of respiration lasts up to eight weeks after birth and its operation is independent of $CO_2$ chemoreceptor function. Fetal respiratory control originates in a different site of the brain than 'post-natal' control of respiration. Second, there are remaining elevated surfactant levels from the fetal state which allows the infant to expire and clear $CO_2$ from the lungs more easily. Third, there are increased closing volumes (from taking first breath). Fourth, there is increased cellular anaerobic capacity remaining from fetal state. This three week time period offers a critical time period in which to diagnose an infant as being predisposed to SIDS and to provide appropriate therapeutic treatment to prevent mortality.

In accord with the invention and in view of the above theory, which is being first disclosed herein, methods and a device for preventing conditions that may lead to the anatomical injury causing SIDS are provided. Also in accord with the invention, in the event such preventative methods and devices are not used (or otherwise effective), diagnostic methods are provided which permit the diagnosis of those infants which have become predisposed to SIDS (i.e., have a high risk for SIDS mortality). Further in accord with the invention, once such predisposed infants are identified, methods, a device and systems thereof are provided to therapeutically treat such predisposed infants to prevent or reduce the mortality of such infants.

Methods and Device for Prevention of SIDS

In accord with the invention, a method of preventing a predisposition to SIDS includes limiting the blood flow (pressure) from the placenta through the umbilical cord to the infant during delivery and preferably also monitoring the adequacy of flow in the umbilical vein.

In accord with one preferred manner of carrying out the invention, a pressure limiting device 10 is placed around the umbilical cord 12 as soon as the umbilical cord is palpable as close to the placenta as possible and preferably before the cord is straightened just after the infant 14 exits the birth canal at the end of labor.

The pressure limiting device 10 preferably includes an inflatable cuff 16 that can be wrapped or applied with a hinge to enable it to encircle the umbilical cord 12. The device is preferably made of a resilient material, e.g., silicone rubber. The device is preferably applied to the umbilical cord as close to the placenta 18 as possible.

Although one cuff is sufficient, the device 10 can include a plurality of cuffs (e.g., on either side of broken line 20). The device 10, in standard operation, restricts the flow of blood from the placenta 18 to the infant 14 but does not cut off the flow of blood completely since the infant needs some placental blood to fill the lungs as they expand to take the first breath.

The device 10 has the ability to be set to a standard limiting pressure (preferably approximately 30 mm Hg) but the pressure can be adjustable at 22, e.g., from zero to 100 mm Hg, and readable from gauge 24 which may be a standard manometer or electrical device. The device preferably includes a sensor 26 or gauge to monitor the adequacy of flow in the umbilical vein prior to cutting the umbilical cord. When the umbilical cord is to be cut, the device 10 can be set so that the pressure of permitted blood flow through the cord 12 is zero.

The device 10 is easy to use. A nurse, midwife, or other practitioner within the delivery or operating room can be trained in its use. The device is removed once the blood has stopped flowing in the umbilical vein or after the cord has been cut.

The device 10 prevents high venous pressure within the infant during the birthing process which can result in inner ear insult as well as injury to other organs that includes the brainstem with consequential predisposition to SIDS.

Methods for Diagnosis of Predisposition for SIDS

In accord with another method of the invention, several tests and clinical observations are provided, the results of which can be used to diagnosis an infant that is predisposed to SIDS.

(A) Tests

1) An elevated blood troponin test can be used to diagnose whether an infant is predisposed to SIDS. Such blood test is given 24 to 48 hours after birth. This test uses venous blood in a general troponin assay (including troponin I and C), which is a marker which would peak at 36 hours after birth. If an infant is predisposed to SIDS, the troponin will be elevated relative to a normal infant due to venous smooth muscle damage. The elevation may be on the level of three fold. Approximately all infants with positive troponin results will have inner ear damage, and the test will pick up ninety percent of babies predisposed to SIDS. The test is inexpensive, easy to perform, and requires minimal training. As such, the test is suitable for use anywhere, particularly including third world countries, where cost, equipment, and practicality are essential considerations. Thus, an elevated troponin test, alone or in combination with other tests described herein, may indicate a predisposition for SIDS.

2) A visual evoked potentials (VEPs) test can be used to diagnose whether an infant is predisposed to SIDS. Such test can be used in the delivery room (or at another location soon after birth) and during a follow-up examination. The optimal time for the initial VEP test is within the first hour after the umbilical cord is cut and more preferably at twenty minutes after the umbilical cord cut, as the effect of the birthing adrenalin surge and inflammation response peaks at this time. This is a sensitive and specific test for the acute significant changes in brain neural activity from the venous pressure damage when compared to a non-SIDS predisposed infant.

This test preferably should be used on all babies at the end of the pediatrician's assessment. The VEP test preferably should be followed-up in ten days. After ten days, there is repair of neural damage tested by the VEP and the test will bear a weaker result. Thus, a VEP test, alone or in combination with other tests described herein, may indicate a predisposition for SIDS.

3) A hearing test can be used to diagnose whether an infant is predisposed to SIDS. The high venous pressure results in damage to the high frequency region of the cochlear hair cells, and this region is most susceptible to hypoxia/ischemia secondary to such damage. A hearing test directed at hearing loss in the 5000-8000 Hz range is a particularly important range as a loss within this frequency range would identify critical damage. Such loss is expected to be bilateral. However, referring to Daniel D. Rubens et al., *Journal of Early Human Development*, Newborn Oto-Acoustic Emission Hearing Screening Tests; Preliminary Evidence For A Marker of Susceptibility to SIDS, Vol. 84:4, pp. 225-229 (April 2008), it is also noted that in view of the anatomy, right-sided hearing loss may be more extensive, and as such hearing loss may be evident on the right side at an even lower frequency range, e.g. 2000-4000 Hz. Thus, appropriate hearing tests, alone or in combination with other tests described herein, may indicate a predisposition for SIDS.

It is also appreciated that a combination of one or more of the above tests can be used in conjunction with other tests to indicate a predisposition for SIDS.

(B) Clinical Diagnosis

In addition to the specific tests indicated above, it is preferable that certain observations be made when making a diagnosis of a predisposition for SIDS.

1) Splinter hemorrhage and bleeding spots in the gums, under the fingernails and/or around the umbilicus. As force equals mass times acceleration (F=MA), the small venules in these areas will suffer increased acceleration and therefore more observable damage. This is indicative of the high venous pressure that also causes inner ear damage.

2) Broken veins in the inside floor of the eyeball (Vena Corticosa), observable within a week after birth, and generally within a few days after birth. This is indicative of the high venous pressure that causes inner ear damage.

3) Cardiac valve injury. This is observable under cardiac echogram. Twenty to thirty percent of SIDS babies have a cardiac valve injury, particularly the tricuspid valve. Such injury is not exclusive to SIDS predisposition, but may indicate a risk.

4) As a single finding, the presence of blood in the mastoid air cells in the absence of any other symptoms or signs suggests SIDS and is unlikely to be caused by anything else. A CT or MRI imaging test can indicate whether fluid (not blood specifically) has entered the mastoid air cells. If the test is positive for fluid, a follow up needle aspirate would demonstrate whether the fluid is blood, confirming the diagnosis of SIDS.

Based on the results of the tests and/or the clinical observations, a diagnosis can be made as to whether the infant is predisposed to SIDS.

Methods, Device & Systems for Treatment of a Predisposition for SIDS

In the event an infant is predisposed to SIDS, in accord with the invention, several methods, a device and systems are provided to treat the infant to prevent mortality of the infant.

The following methods, device and systems are based, as discussed above, on the theory that information concerning $CO_2$ levels is transmitted from the peripheral carotid chemoreceptors to the brainstem via the vestibular hair cells in the inner ear. Furthermore, the theory holds that the predisposition for SIDS is due to a perinatal placental transfusion injury that results in damage to the inner ear vestibular hair cells and brainstem central $CO_2$ chemoreceptor cells. However, such methods, device and systems may still be useful for therapeutic effect even if the functional pathway giving rise to a SIDS predisposition is other than exactly theorized. The proposed theory underlying the invention is that SIDS and its known association with established risk factors can be explained by an infant's critical inability to detect and therefore respond to hypercarbia as a result of a perinatal injury. If the inability to detect and respond to hypercarbia is due to a different injury or a non-injury cause, the methods, device and systems may still operate to regulate respiration and $CO_2$ levels to prevent harmful $CO_2$ accumulation. It is also recognized that such methods, device and systems may have application in the treatment of other conditions requiring auditory stimulation and/or the prevention of hypercarbia.

Notwithstanding the potential larger application, the methods, devices and systems of the invention will be described with reference to the treatment of an infant predisposed to SIDS. To provide additional context for the methods, devices and systems for treatment of a predisposition to SIDS, additional detail of the theory is provided.

The sleep period is an especially vulnerable period since respiration is depressed (slowed and shallow) at this time. The wakeful state is protective since an adequate level of respiration is maintained to clear $CO_2$ at this time even in the presence of inner ear damage due to the level of arousal of the brain at this time.

In contrast to $CO_2$, $PaO_2$ (the partial pressure of oxygen within the blood) information is transmitted directly from the carotid chemoreceptors to the brainstem and this pathway is relatively intact following a placental transfusion injury. The increase in respiratory rate and decrease in heart rate that will occur with a drop in $PaO_2$ may therefore be the earliest signs of a pending SIDS event. A decrease in cerebral oxygenation due to the drop in $PaO_2$ may also be an early warning sign. The respiratory response invoked by a drop in $PaO_2$ is shallow breathing which is incapable of removing the quantities of $CO_2$ that will have accumulated in the systemic circulation and lungs by this time.

Hyperthermia of any cause will precipitate an elevation in systemic $CO_2$ levels since metabolic rate increases with increasing temperature. An increase in core temperature or the core-peripheral temperature gradient (at a time that core temperature is rising) will therefore be another early warning of $CO_2$ accumulation.

In addition to providing the brain with information from the carotid bodies concerning lung removal of $CO_2$, the vestibular hair cells provide the brain with information regarding mixed venous $CO_2$ ($MVCO_2$) levels which is transmitted to the inner ear from middle ear chemoreceptors. The $MVCO_2$ information is conveyed from the inner ear to the brain in order to provide the hypothalamus with feedback regarding the basal metabolic rate. The lack of useful $CO_2$ information due to the inner ear damage leads the brain to believe that metabolism is stagnant, with the result that the hypothalamus stimulates metabolism even further, resulting in even greater $CO_2$ production. The vestibular hair cells in the inner ear can therefore be described as a transmission station for information regarding $CO_2$ production and removal. The vestibular hair cells portray changes in $CO_2$ levels by signaling to the brain via neuronal pathways the comparison of the respiratory response to $CO_2$ levels with the metabolic production of $CO_2$, allowing the brain to make a comprehensive assessment of $CO_2$ information and to respond in relation to the respiratory or metabolic requirements.

In the face of unremitting hypercarbia, oxygen will be unloaded from hemoglobin even in the lungs and the shallow respiratory response to decreasing $PaO_2$ is inadequate to remove $CO_2$ and replenish the alveoli with oxygen. Consequently, the diving reflex will be activated when the preBotzinger complex stops firing from the effects of profound hypoxia and hypercarbia. The diving reflex response includes apnea, vocal cord closure, central vasoconstriction and suppression of metabolism. It is also known as the oxygen conserving reflex response. The preBotzinger complex region of the brain is responsible for respiration regulation.

Activation of the diving reflex is a terminal point in a SIDS infant, since conventional resuscitation measures only drive more $CO_2$ into the system after this point and the infant is unable to recommence respiration and break the reflex due to the lack of useful information about $CO_2$ levels. Contrary to the non-SIDS situation, $CO_2$ production continues to increase in SIDS even after the diving reflex is activated due to the lack of information being transmitted to the brain from the inner ear concerning $MVCO_2$ levels.

The gasp reflex is only activated when the $PaO_2$ decreases to 5-15 mm Hg and there is inadequate anaerobic capacity in the heart and brain for the SIDS infant to survive until and beyond this point after one month of age.

In order to monitor and respond to biological activity that may otherwise result in a SIDS episode, the following methods and treatment device 100 should be made available to infants susceptible to SIDS by approximately two to three weeks after birth.

The treatment device 100 should include the following subsystems: a stimulation system such as an auditory stimulation system 102, a neural stimulation system 118, a monitoring system 104, a warming system 106, and a response system 108. While it is preferred that all subsystems of the treatment device 100 be provided as components of an integrated treatment system, it is appreciated that the individual subsystem can be separately used and configured to work in accord with the general method described with respect to the treatment system and that while all subsystem components are preferred, a subset of the subsystems and parts thereof may be provided.

(A) Stimulation Systems

An auditory stimulation system 102 includes one or more auditory stimulus files, a storage device 110 storing the stimulus files, an audio playback device 112 to playback the stimulus files on the storage device.

Each auditory stimulus file includes digital or analog audio data, i.e., the information necessary for the audio playback device to generate audio and preferably music that provides an auditory stimulus to a SIDS predisposed infant which operates to regulate respiration during sleep. The generated audio is a non-random, logical arrangement of tones or notes. The notes are preferably melodically arranged in scales with crescendos. The arrangements are preferably active, but not complex. A preferred note arrangement is based around the mixolydian mode, the note arrangement of which is a major scale with a chord underneath, providing natural harmony to the arrangement. It is also preferable that instruments or electronic sounds be used in auditory valuable frequencies. By way of example, low frequency and ultra low frequency instruments can be heard even if there is auditory damage that limits higher frequency audition. That is, the frequencies reproduced should particularly include tones outside the range of potential disruption (2000-4000 Hz and 5000-8000 Hz). One preferred instrument for lower frequency sounds is a double bass accompanied by a mid-register sound such as that produced by an organ. A percussive beat should preferably be kept to approximate the heart rate (approximately 50-60 beats per minute). Certainly other options and combinations of instruments can be used. There are preferably multiple arrangements of three to seven minutes in duration on the storage device 110 for playback in sequence, in random, or a user selected order.

The storage device 110 may be digital media, including a removable memory chip device (i.e., on a card or a USB storage device) or memory device permanently integrated into the audio playback device 112, or an optical storage carrier, e.g., a compact disc or digital versatile disc. The storage device 110 may also be analog media including a cassette tape or a vinyl record.

It is appreciated that the generated audio also may be generated by the audio playback device 112 (as opposed to 'playback' of files stored on memory) based upon a set of rules for the generation of such audio. Such rules function as auditory stimulus files, and the location of such rules is the storage device. Whether the audio is reproduced from stored files or produced directly by the device 112, the terms 'produced', 'reproduced' and 'playback' are considered to be interchangeable for purposes herein.

Regardless of the form of the stimulus file, the audio playback device 112 integrates with the storage device 110 to allow reading of the digital or analog information relating to the stimulus file and playback thereof. The audio playback device 112 includes electroacoustic transducers (e.g., loudspeakers, headphones, earphone, etc.) or connections (wired or wireless) for coupling at least one electroacoustic transducer thereto. In a preferred embodiment, earphones 114 coupled to the playback device 112 are adhered (via a glue) within at least one and preferably both ear canals of the infant 116 during use and more preferably during the entire critical time period in which the therapeutic system is being used, e.g., three weeks to six months.

The auditory stimulation device 102 can be manually activated for use whenever the infant 116 may enter a sleep state; i.e., during night time, nap time, etc. In addition or alternatively, the auditory stimulation device 102 can be set to be automatically activated upon signal from the monitoring system when the respiratory rate and pulse rate decrease to a set level as the infant falls asleep. Then, if and when the monitoring system 104 identifies signals below a predetermined critical threshold, the monitoring system 104 sends a signal to the auditory stimulus device 102 that initiates (or continues) playback of the music related to the stimulus file.

In addition to or alternatively to the auditory stimulation device 102, a neural stimulation device 118 is optionally provided. The neural stimulation device 118 transmits a continuous electromagnetic signal at a predetermined frequency. The predetermined frequency amplifies a specific frequency that functions as a carrier signal for the neural pathways of the infant. The neural pathways targeted are those that have specifically been damaged by the birthing injury, and more specifically those in the inner ear and brainstem which are required for transmission of $CO_2$ information as well as the pathways that trigger the diving and gasp reflexes.

The signals transmitted via the damaged neural pathways are not completely disrupted and some signals do get through in SIDS infants at baseline. By amplifying the predetermined frequency signal, there is an increase in the likelihood of adequate useful transmission via the damaged vital nerve pathways so a crisis state can be prevented.

(B) The Monitoring System

The monitoring system 104 preferably includes a heart rate monitor 120, two $CO_2$ monitors 122, 124, a respiration rate monitor 126, a core temperature monitor 128, a peripheral axillary temperature monitor 129 and a cerebral oximeter 130. The heart rate monitor 120 identifies decreased heart rate which is related to hypoxemia secondary to vocal cord closure. A first $CO_2$ monitor 122 is a transcutaneous $CO_2$ monitor to measure a rise in blood $CO_2$. A second $CO_2$ monitor 124 is an environmental $CO_2$ monitor preferably positionable approximate to the head of the infant. The environmental $CO_2$ monitor 124 identifies elevated $CO_2$ earlier than the transcutaneous monitor. When blood $CO_2$ finally rises, the surrounding environmental $CO_2$ already has been elevated for some time. Vocal cords close after a dangerous rise in blood $CO_2$ (i.e., as part of the diving reflex (DR)) which occurs later than the rise in ambient or environmental $CO_2$ around the infant's head. It is therefore important to detect a rise in environmental $CO_2$ early. The respiration rate monitor 126 identifies increased respiration which is indicative of shallow breaths with increased $CO_2$ and decreased $PaO_2$. The core temperature monitor 128 provides the temperature relative to the peripheral temperature taken at the axilla via axillary temperature monitor 129. The core temperature is preferably taken from within the inner ear close to the tympanic membrane which is indicative of the core (carotid artery) temperature. The temperature sensor of the core temperature monitor 128 may be integrated within an earphone 114 of the auditory stimulus system 102. The cerebral oximeter 130 is preferably a near-infrared sprectrophotometry cerebral oximeter that can detect an early drop in brain oximetry.

The monitoring system may also include a ketone level monitor which is preferably incorporated into the environmental $CO_2$ monitor 124. Decreased breath ketones would give an early warning of a pending SIDS crisis. Ketones could be detected by a breath analyzer. Similarly, the monitor can be used as a diagnostic tool for testing breath ketone levels following three weeks after birth in the sleeping state. Ketone bodies are created at moderate levels in everyone's bodies during sleep when no carbohydrates are available. Ketone production is decreased in SIDS babies due to liver damage.

The heart rate monitor 120 and the $CO_2$ monitors 122, 124 can indicate that a SIDS condition crisis is occurring. All the monitors 124-130 provide an indication that a SIDS condition may be pending.

All of the monitors may be provided in wired or wireless configurations and a wireless system is preferable. In a wireless configuration, respective sensors wirelessly transmit their data to one or more stations of the monitoring system. In this manner, fewer wired connections are required to be maintained directly to the infant to permit the infant greater comfort and mobility.

(C) Warming System

The warming system 106 includes an enclosure 140 with circulating fluid (air or water) (e.g., via inlet 142 and outlet 144), and an insulated suit 146 that is worn by the infant. The circulating fluid is preferably warmed. The suit 146 and warm fluid are adapted to keep the infant's core body temperature at an approximately constant temperature, preferably 37° C.±0.5° C. It is preferable that the head of the infant be situated outside the suit to prevent overheating.

(D) Response System

The response system 108 is used in response to a crisis occurring or crisis pending situation. The response system 108 include an oxygen delivery system 150, a racaemic epinephrine delivery system 152, and a cooling system 154. The oxygen delivery system 150 delivers oxygen to clear $CO_2$ from the lungs. The device will deliver a continual background flow of oxygen and will have the capacity to deliver additional bursts when a crisis is detected; such as when the heart rate drops by predetermined level, e.g., twenty percent from baseline or to less than 80 beats per minute, or the respiratory rate increases to a predetermined threshold level, e.g., a fifteen percent increase from baseline or greater than 45 breaths per minute. The epinephrine delivery system 152 provides racemic epinephrine in a manner which facilitates pumping the heart to remove $CO_2$ from the lungs. The racemic epinephrine is delivered from close to the head of the infant via an inhalable aerosol spray system or otherwise so that it reaches the airway or nasal passages of the infant.

The cooling system 154 may be integrated within the suit. The cooling system 154 includes channels 156 for cooled liquid, air, or solids to reduce the temperature of a particular anatomical location of the infant. A preferred location is the back of the neck 158. An infant undergoing a SIDS crisis needs to be triggered out of the diving reflex (DR). Cooling the neck 158 breaks the diving reflex (DR) and instigates the gasp reflex (GR). The reason is that cooling the neck will cool the brainstem which 'tricks' the area that controls the gasp reflex into believing the $PaO_2$ is 5-15 mm Hg; much before the $PaO_2$ actually drops this low. The effect is that the infant will make continual gasps at an earlier time than would otherwise be activated. The best time to activate cooling of the neck is when the $CO_2$ levels rise suddenly (e.g., increase by more than ten percent relative to baseline or to greater than 55 mmHg) and the vocal cords close indicated by a substantial decrease in heart rate and/or increase in respiratory rate. This is the point of DR activation. This point can be identified from the respective monitors 104 and the response system 108 can be automatically activated. The cooling system 154 can be additionally or alternatively applied to another anatomical location that will trigger the infant out of the diving reflex and instigate the gasp reflex.

The response system 108 needs to ignore normal behavior yet respond to changes indicative of a pending or occurring crisis. The infant 116 needs to breathe on its own (and not artificially) unless there is an emergency. Yet the therapeutic device 100 needs to monitor and immediately recognize when there is a serious problem and respond by activation of the response system 108 instantly when there is an emergency. It therefore requires sensitive monitoring equipment that will activate the system response, yet not respond to false alarm data, e.g., if the infant turns over or stops breathing for a few seconds.

There have been described and illustrated herein embodiments of methods, devices and systems related to the prevention, diagnosis and treatment of a predisposition to SIDS. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A treatment system for treating an infant previously diagnosed as predisposed to Sudden Infant Death Syndrome (SIDS), the infant having a brainstem adjacent a back of a neck, comprising:

a) an auditory stimulation system that reproduces a specific melodic and harmonic arrangement of tones in a mixolydian mode through at least one sound transducer to stimulate the auditory system of the infant;

b) a monitoring system including,
   i) a heart rate monitor that monitors a heart rate of the infant, and
   ii) a first $CO_2$ monitor that measures a blood $CO_2$ of the infant;

c) a warming system that maintains a body of the infant at a substantially constant core temperature; and d) a response system activated when the monitoring system indicates that there is a decrease in the heart rate and an increase in the blood $CO_2$ associated with activation of a diving reflex, the response system including,
   i) an oxygen delivery system to deliver inhalable oxygen to the infant,
   ii) an epinephrine delivery system to deliver inhalable epinephrine to the infant, and
   iii) a cooling system to cool a portion of the infant,
   wherein the warming system and the cooling system are integrated within a common suit for the infant, and a portion of the cooling system within the suit is located for placement at the back of the neck of the infant to sufficiently cool the brainstem of the infant to interrupt the diving reflex and to initiate a gasp reflex and thereby increase a partial pressure of oxygen in the blood of the infant.

2. A treatment system according to claim 1, wherein:
said at least one sound transducer of said auditory system includes a pair of earphones that are couplable directly to the ears of the infant.

3. A treatment system according to claim 1, wherein:
said auditory stimulation system is automatically activated to reproduce said tones upon signal from said monitoring system.

4. A treatment system according to claim 1, wherein:
said monitoring system further includes a second $CO_2$ monitor that measures environmental $CO_2$ proximate the infant.

5. A treatment system according to claim 1, wherein:
said monitoring system further includes a respiration rate monitor that identifies increased respiration of the infant, said response system activated by an increase in respiration rate to above a predetermined level.

6. A treatment system according to claim 1, wherein:
said monitoring system further includes a core temperature monitor to measure the core temperature of the infant,
a peripheral temperature monitor to measure the peripheral temperature of the infant, such that the core and peripheral temperatures can be compared relative to each other, and
a cerebral oximeter to detect a drop in brain oximetry in the infant.

7. A treatment system according to claim 1, wherein:
said warming system includes an enclosure through which a warming fluid is circulated.

8. A treatment system according to claim 1, wherein:
said cooling system provides sufficient cooling to the brainstem to cause the brainstem to interpret that the partial pressure of oxygen in the blood is lower than it actually is.

9. A treatment system for treating an infant previously diagnosed as predisposed to Sudden Infant Death Syndrome (SIDS), the infant having a brainstem adjacent at back of a neck, comprising:
a) a monitoring system including,
   i) a heart rate monitor that monitors a heart rate of the infant, and
   ii) a first $CO_2$ monitor that measures a blood $CO_2$ of the infant, and
   iii) a cerebral oximeter to detect a drop in brain oximetry in the infant; and b) a warming system that maintains a body of the infant at a substantially constant core temperature; and c) a response system activated when the monitoring system indicates that there is a decrease in the heart rate and an increase in the blood $CO_2$ and decrease in brain oximetry associated with activation of a diving reflex, the response system including,
   i) an oxygen delivery system to deliver inhalable oxygen to the infant, and
   ii) a cooling system to cool a portion of the infant,
   wherein the warming system and the cooling system are integrated within a common suit for the infant, and a portion of the cooling system within the suit is located for placement at the back of the neck of the infant to cool the brainstem of the infant to interrupt the diving reflex and to initiate a gasp reflex and thereby increase a partial pressure of oxygen in the blood of the infant.

10. A treatment system according to claim 9, wherein:
said monitoring system further includes a second $CO_2$ monitor that measures environmental $CO_2$ proximate the infant.

11. A treatment system according to claim 9, wherein:
said monitoring system further includes a respiration rate monitor that identifies increased respiration of the infant, said response system activated by an increase in respiration rate to above a predetermined level.

12. A treatment system according to claim 9, wherein:
said monitoring system further includes a core temperature monitor to measure the core temperature of the infant, and
a peripheral temperature monitor to measure the peripheral temperature of the infant, such that the core and peripheral temperatures can be compared relative to each other.

13. A treatment system according to claim 9, wherein:
said response system includes an epinephrine delivery system to deliver inhalable epinephrine to the infant.

14. A treatment system according to claim 9, wherein:
said cooling system provides sufficient cooling to the brainstem to cause the brainstem to interpret that the partial pressure of oxygen in the blood is lower than it actually is.

15. A stimulation system for an infant predisposed to Sudden Infant Death Syndrome (SIDS), the infant having an auditory system, and the stimulation system for use with a monitoring system including a heart rate monitor and a temperature sensor, comprising:
an auditory stimulation system including an earphone having at least one sound transducer and the temperature sensor of the monitoring system integrated into the earphone for placement within an ear canal of the infant, the auditory system, when activated, produces a melodic and harmonic arrangement of tones in a mixolydian mode and outside the range of 2000-4000 Hz and outside the range of 5000-8000 Hz, said tone emitted through the at least one sound transducer to stimulate the auditory system of the infant, said auditory stimulation system including an input to receive a signal from the heart rate monitor such that when said auditory stimulation system receives a signal from the heart rate monitor indicating that the infant heart rate has reached a predetermined rate, the auditory stimulation system is automatically activated.

16. A stimulation system according to claim 15, wherein: said tones are accompanied by a percussive beat of 50-60 beats per minute.

* * * * *